(12) United States Patent
Tanaka et al.

(10) Patent No.: US 11,774,114 B2
(45) Date of Patent: Oct. 3, 2023

(54) AIR TREATMENT DEVICE

(71) Applicant: DAIKIN INDUSTRIES, LTD., Osaka (JP)

(72) Inventors: Hidekazu Tanaka, Osaka (JP); Ryuuji Akiyama, Osaka (JP); Kei Suzumura, Osaka (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 17/872,075

(22) Filed: Jul. 25, 2022

(65) Prior Publication Data

US 2022/0357054 A1    Nov. 10, 2022

Related U.S. Application Data

(63) Continuation of application No. PCT/JP2021/004617, filed on Feb. 8, 2021.

(30) Foreign Application Priority Data

Feb. 7, 2020   (JP) .................................. 2020-019828

(51) Int. Cl.
*F24F 1/02* (2019.01)
*A61L 2/10* (2006.01)
(Continued)

(52) U.S. Cl.
CPC ....... *F24F 1/02* (2013.01); *A61L 2/10* (2013.01); *F24F 1/0018* (2013.01); *A61L 9/00* (2013.01);
(Continued)

(58) Field of Classification Search
CPC ...... F24F 1/0018; F24F 1/0035; F24F 1/0071; F24F 1/008; F24F 1/02; F24F 1/028;
(Continued)

(56) References Cited

U.S. PATENT DOCUMENTS

| 5,330,722 A | * | 7/1994 | Pick ......................... A61L 9/16 250/492.1 |
| 5,783,117 A | * | 7/1998 | Byassee .................. F24F 6/043 261/107 |

(Continued)

FOREIGN PATENT DOCUMENTS

| JP | 64-38532 A | 2/1989 |
| JP | 2003-83594 A | 3/2003 |

(Continued)

OTHER PUBLICATIONS

International Preliminary Report on Patentability and English translation of the Written Opinion of the International Searching Authority (Forms PCT/IB/338, PCT/IB/373 and PCT/ISA/237) for International Application No. PCT/JP2021/004617, dated Aug. 18, 2022.

(Continued)

*Primary Examiner* — Binh Q Tran
(74) *Attorney, Agent, or Firm* — Birch, Stewart, Kolasch & Birch, LLP (57) ABSTRACT

An air treatment device includes: a casing having an inlet through which air is drawn, and an outlet out of which the air drawn through the inlet is blown; a blade configured to adjust a direction of the air blown out of the outlet; and a generator configured to generate an antimicrobial element that sanitizes the blade. The blade has a first surface, and a second surface opposite to the first surface. The blade is shiftable between a first position in which the antimicrobial element is provided to the first surface and a second position in which the antimicrobial element is provided to the second surface.

16 Claims, 8 Drawing Sheets

(51) Int. Cl.

| | | |
|---|---|---|
| *F24F 1/0018* | (2019.01) | |
| *F24F 1/028* | (2019.01) | |
| *F24F 1/008* | (2019.01) | |
| *F24F 1/0328* | (2019.01) | |
| *F24F 1/0035* | (2019.01) | |
| *F24F 3/16* | (2021.01) | |
| *F24F 1/0071* | (2019.01) | |
| *F24F 1/0355* | (2019.01) | |
| *F24F 8/40* | (2021.01) | |
| *F24F 8/24* | (2021.01) | |
| *F24F 8/50* | (2021.01) | |
| *F24F 8/20* | (2021.01) | |
| *A61L 101/00* | (2006.01) | |
| *A61L 101/34* | (2006.01) | |
| *A61L 9/00* | (2006.01) | |
| *A61L 9/01* | (2006.01) | |

(52) U.S. Cl.
CPC ............ *A61L 9/01* (2013.01); *A61L 2101/00* (2020.08); *A61L 2101/34* (2020.08); *A61L 2202/10* (2013.01); *A61L 2202/14* (2013.01); *A61L 2202/15* (2013.01); *A61L 2209/10* (2013.01); *A61L 2209/21* (2013.01); *A61L 2209/211* (2013.01); *F24F 1/008* (2019.02); *F24F 1/0035* (2019.02); *F24F 1/0071* (2019.02); *F24F 1/028* (2019.02); *F24F 1/0328* (2019.02); *F24F 1/0355* (2019.02); *F24F 3/16* (2013.01); *F24F 8/20* (2021.01); *F24F 8/24* (2021.01); *F24F 8/40* (2021.01); *F24F 8/50* (2021.01); *F24F 2221/22* (2013.01)

(58) Field of Classification Search
CPC .... F24F 2221/22; F24F 1/0328; F24F 1/0355; F24F 3/16; F24F 8/20; F24F 8/22; F24F 8/24; F24F 8/40; F24F 8/50; F24F 8/80; F24F 11/65; F24F 2013/228; A61L 2/10; A61L 9/00; A61L 9/01; A61L 9/015; A61L 2101/00; A61L 2101/34; A61L 2202/00; A61L 2202/10; A61L 2202/14; A61L 2202/15; A61L 2209/00; A61L 2209/10; A61L 2209/11; A61L 2209/14; A61L 2209/16; A61L 2209/21; A61L 2209/211; A61L 2209/212; A61L 9/20

See application file for complete search history.

(56) References Cited

U.S. PATENT DOCUMENTS

| | | | |
|---|---|---|---|
| 11,365,929 B1* | 6/2022 | Marinelli | F24F 13/222 |
| 2008/0295271 A1* | 12/2008 | Perunicic | A47L 11/405 |
| | | | 15/246.3 |
| 2016/0067363 A1* | 3/2016 | Robert | A61L 2/14 |
| | | | 315/111.81 |
| 2021/0148584 A1* | 5/2021 | Barlettano | F24F 5/0035 |
| 2021/0372637 A1* | 12/2021 | Sharma | F24F 8/158 |

FOREIGN PATENT DOCUMENTS

| | | |
|---|---|---|
| JP | 2009-85576 A | 4/2009 |
| JP | 2014-126303 A | 7/2014 |
| JP | 2016-217582 A | 12/2016 |
| JP | 2017-213263 A | 12/2017 |

OTHER PUBLICATIONS

International Search Report, issued in PCT/JP2021/004617, dated Mar. 23, 2021.
Written Opinion of the International Searching Authority, issued in PCT/JP2021/004617, dated Mar. 23, 2021.

* cited by examiner

AIR TREATMENT DEVICE

CROSS REFERENCE TO RELATED APPLICATIONS

This application is a Continuation of PCT International Application No. PCT/JP2021/004617, filed on Feb. 8, 2021, which claims priority under 35 U.S.C. 119(a) to Patent Application No. 2020-019828, filed in Japan on Feb. 7, 2020, all of which are hereby expressly incorporated by reference into the present application.

TECHNICAL FIELD

The present disclosure relates to an air treatment device.

BACKGROUND ART

An air conditioner serving as a type of air treatment device has been known in the art. Patent Document 1 discloses an air conditioner having the function of maintaining its internal cleanliness. Specifically, the air conditioner of Patent Document 1 includes an indoor unit. The indoor unit includes a heat exchanger, a fan, an air flow path from an inlet to an outlet, upper and lower flaps (blades), and a sprayer. The upper and lower flaps are provided at the outlet. The sprayer atomizes water.

In the indoor unit, the upper and lower flaps turn to close the outlet, and water with antimicrobial activity is sprayed from the sprayer into the air flow path of the indoor unit. The water with antimicrobial activity is supplied to the heat exchanger and the fan.

CITATION LIST

Patent Documents

Patent Document 1: Japanese Unexamined Patent Publication No. 2009-85576

SUMMARY

A first aspect of the present disclosure is directed to an air treatment device (100) including: a casing (11) having an inlet (11a) through which air is drawn, and an outlet (11b) out of which the air drawn through the inlet (11a) is blown; and a blade (21) configured to adjust a flow direction of the air blown out of the outlet (11b). The air treatment device (100) further includes: a generator (32) configured to generate an antimicrobial element that sanitizes the blade (21). The blade (21) has a first surface (23), and a second surface (24) opposite to the first surface (23). The blade (21) is shiftable between a first position in which the antimicrobial element is provided to the first surface (23) and a second position in which the antimicrobial element is provided to the second surface (24).

DESCRIPTION OF EMBODIMENTS

First Embodiment

—General Configuration of Air Conditioner—

An air treatment device according to a first embodiment is an air conditioner (100) that adjusts the indoor temperature. The air conditioner (100) adjusts the temperature of indoor air, and supplies the temperature-adjusted air as supply air into a room. The air conditioner (100) includes an indoor unit (1) installed indoors, and an outdoor unit installed outdoors.

The indoor unit (1) is connected to the outdoor unit (not shown) via a refrigerant pipe. Thus, in the air conditioner (100), a refrigerant circuit is formed. The refrigerant circuit is filled with a refrigerant which circulates to perform a vapor compression refrigeration cycle. The outdoor unit includes a compressor and an outdoor heat exchanger both connected to the refrigerant circuit, and an outdoor fan corresponding to the outdoor heat exchanger.

—Configuration of Indoor Unit—

Figure 1:
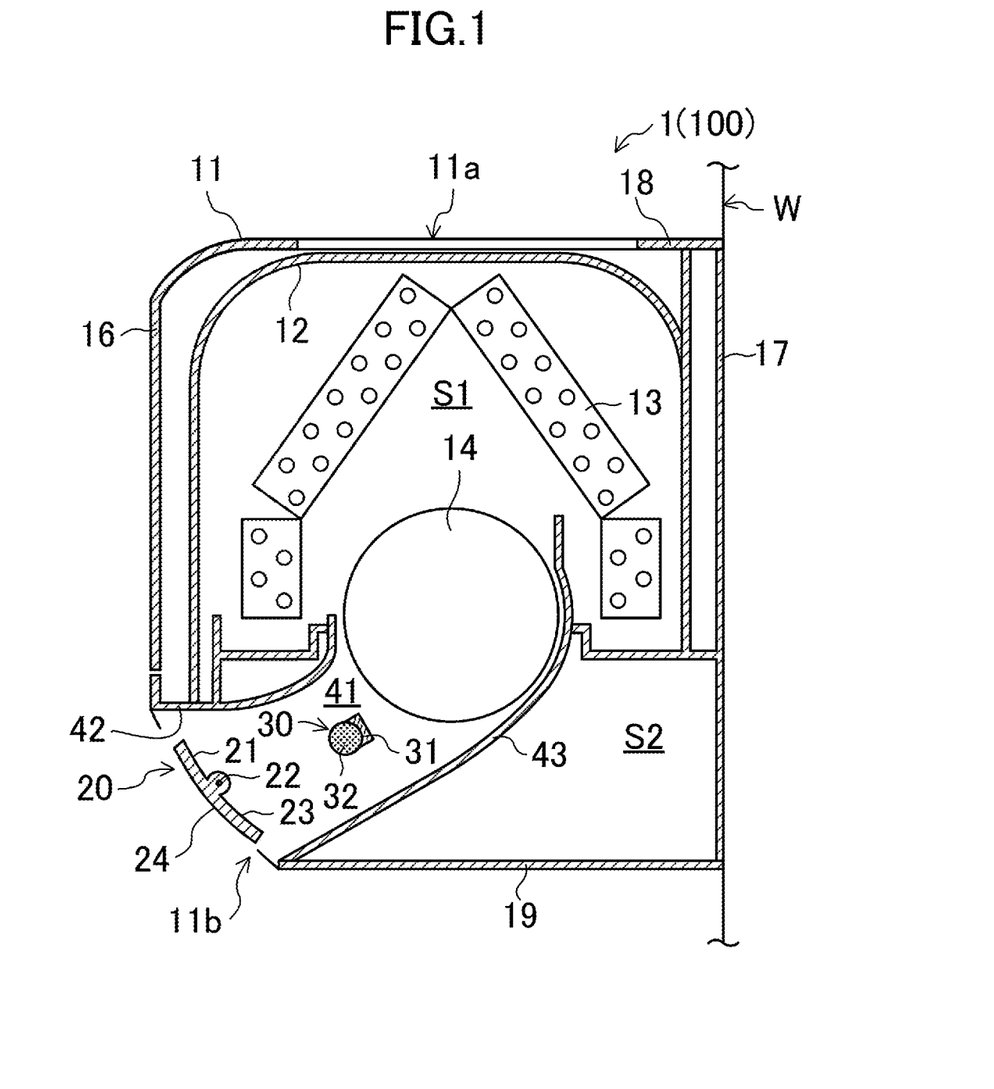
FIG. 1 is a vertical sectional view illustrating a configuration of an indoor unit according to a first embodiment.

The indoor unit (1) is provided in a room to be air-conditioned. As illustrated in FIG. 1, the indoor unit (1) includes a casing (11), a filter (12), a heat exchanger (13), a fan (14), a flow path forming portion (40), a flap (20), a generation unit (30), and a control unit (15). In FIG. 1, the control unit (15) is not shown. The terms "upper," "top," "lower," "bottom," "right," "left," "front," and "rear" in the following description refer to the directions when the indoor unit (1) is viewed from the front.

<Casing>

As illustrated in FIG. 1, the casing (11) is attached to a wall (W) of the room to be air-conditioned. The casing (11) is formed in a hollow rectangular parallelepiped shape that is laterally long as viewed from the front. The casing (11) is mainly made of a resin. An internal space (S1) is formed in the casing (11) to house the filter (12), the heat exchanger (13), the fan (14), and the generation unit (30).

The casing (11) includes a front panel (16), a rear panel (17), a top panel (18), and a bottom panel (19). The front panel (16) forms a front surface of the casing (11). The rear panel (17) forms a rear surface of the casing (11). The top panel (18) forms a top surface of the casing (11). The front end of the top panel (18) is connected to the upper end of the front panel (16), and the rear end of the top panel (18) is connected to the upper end of the rear panel (17). The bottom panel (19) forms a bottom surface of the casing (11). The front end of the bottom panel (19) is connected to the lower end of the front panel (16), and the rear end of the bottom panel (19) is connected to the lower end of the rear panel (17).

The casing (11) has an inlet (11a) and an outlet (11b). The inlet (11a) is an opening through which indoor air is to be introduced into the internal space (S1) of the casing (11). The inlet (11a) is formed in an upper portion of the casing (11). The inlet (11a) is formed in the top panel (18). The inlet (11a) is an opening formed in the shape of a rectangle with the long sides oriented along the lengthwise direction of the top surface of the casing (11) and the short sides oriented along the widthwise direction of the top surface of the casing (11). The inlet (11a) is formed along the lengthwise direction of the casing (11).

The outlet (lib) is an opening through which air that has passed through the heat exchanger (13) is to be led out of the casing (11). The outlet (11b) is formed in a lower portion of the casing (11). The outlet (lib) is formed in the bottom panel (19). The outlet (lib) is an opening formed in the shape of a rectangle with long sides oriented along the lengthwise direction of the bottom surface of the casing (11) and short sides oriented along the widthwise direction of the bottom surface of the casing (11). The outlet (lib) is formed along the lengthwise direction of the casing (11).

<Filter>

The filter (12) is disposed between the inlet (11a) and the heat exchanger (13). The filter (12) faces the inlet (11a). The filter (12) catches dust and any other substances in the air drawn through the inlet (11a) into the casing (11).

<Heat Exchanger>

The heat exchanger (13) is a so-called "cross-fin-type" heat exchanger. The heat exchanger (13) is disposed in an upper portion of the interior of the casing (11). The heat exchanger (13) is opposed to the circumferential surface of the fan (14). Specifically, the heat exchanger (13) is disposed to surround the front, upper, and rear sides of the fan (14). The heat exchanger (13) is connected to the refrigerant circuit (not shown) via pipes (not shown). The heat exchanger (13) exchanges heat between the refrigerant flowing through the refrigerant circuit and indoor air.

<Fan>

The fan (14) is a so-called "cross-flow fan." The fan (14) has an elongated cylindrical shape. The fan (14) is configured to be rotatable around its axis generally parallel to the lengthwise direction of the casing (11). The fan (14) is driven to rotate by a fan motor (not shown). The fan (14) draws the air that has flowed into the casing (11) to pass through the heat exchanger (13), and blows the drawn air toward the outlet (11b). The fan (14) sends the air conditioned by the heat exchanger (13) out of the outlet (11b) into the room.

<Flow Path Forming Portion>

The flow path forming portion (40) forms a blow-out flow path (41) in the shape of a scroll between the fan (14) and the outlet (11b). The flow path forming portion (40) includes a front side wall (42) and a rear side wall (43). The front and rear side walls (42) and (43) are made of a resin.

The front side wall (42) is disposed in front of the fan (14). Specifically, the front side wall (42) is disposed between the fan (14) and the front panel (16). The front side wall (42) faces a front portion of the blow-out flow path (41).

The rear side wall (43) is disposed toward the rear of the fan (14). Specifically, the rear side wall (43) is disposed between the fan (14) and the rear panel (17) and between the fan (14) and the bottom panel (19). The rear side wall (43) faces a rear portion of the blow-out flow path (41). The rear side wall (43) is gently curved along the blow-out flow path (41). The rear side wall (43) is formed from an upper part of the fan (14) to the outlet (11b).

A pipe space (S2) is formed between a lower portion of the rear panel (17) of the casing (11) and the rear side wall (43). A refrigerant pipe for the refrigerant circuit, a discharge path (e.g., a hose) for condensed water, and other components are housed in the pipe space (S2). The control unit (15) is further housed in the pipe space (S2).

<Flap>

The flap (20) corresponds to a blade. The flap (20) adjusts the flow direction of the air blown out of the outlet (11b). The single flap (20) is provided at the outlet (11b) of the casing (11). The flap (20) is configured to be capable of opening and closing the outlet (11b). The flap (20) includes a flap body (21) and a shaft (22).

The flap body (21) is a rectangular plate-shaped blade member with the long sides oriented along the lengthwise direction of the outlet (11b) and the short sides oriented along the widthwise direction of the outlet (11b). The long sides of the flap body (21) are oriented along the lengthwise direction of the casing (11).

The shaft (22) is provided on the center of the flap body (21) to be generally parallel to the lengthwise direction of the flap body (21). In other words, the shaft (22) is disposed on the center of the outlet (11b). The flap body (21) is driven to rotate around the shaft (22) by a flap motor (not shown). FIG. 1 illustrates a state where the flap body (21) blocks the outlet (11b).

The flap body (21) has a first surface (23) and a second surface (24) opposite to the first surface (23). The first surface (23) is a surface facing the inside of the casing (11) while the air conditioner (100) is at rest. The second surface (24) is a surface facing the outside of the casing (11) while the air conditioner (100) is at rest.

Figure 4:
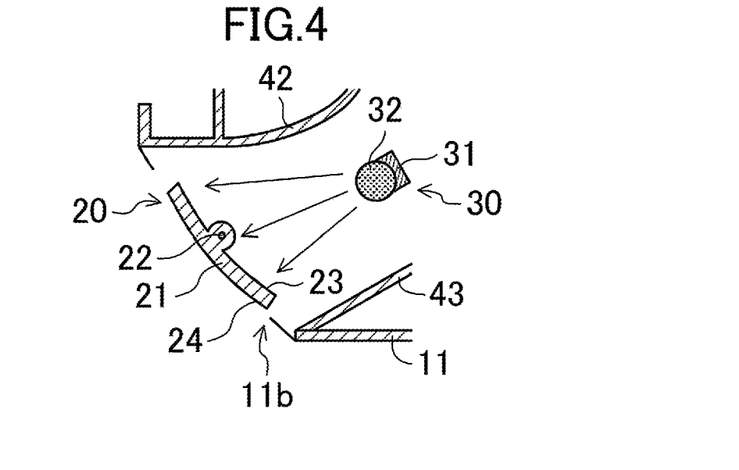
FIG. 4 is an explanatory diagram illustrating the state of a flap in a first position.
Figure 6:
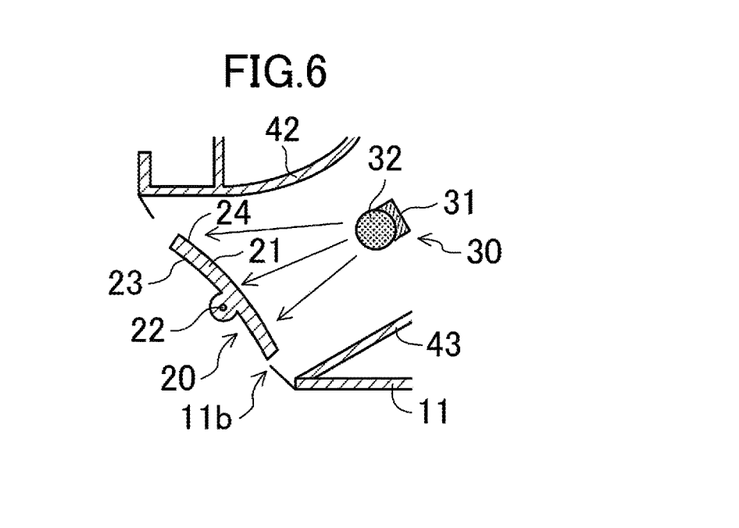
FIG. 6 is an explanatory diagram illustrating the state of the flap in the second position.

The flap body (21) is configured to rotate around the shaft (22) so as to be shiftable between first and second positions. As illustrated in FIG. 4, the first position is a position in which the first surface (23) of the flap body (21) faces the inside of the casing (11). In the first position, the first surface (23) of the flap body (21) faces a plurality of generators (32), which will be described below. As illustrated in FIG. 6, the second position is a position in which the second surface (24) of the flap body (21) faces the inside of the casing (11). This second position is a position in which the flap body (21) is rotated by 180° from the first position. In the second position, the second surface (24) of the flap body (21) faces the generators (32), which will be described below. In the first and second positions, the flap (20) blocks the outlet (11b).

<Generation Unit>

Figure 2:
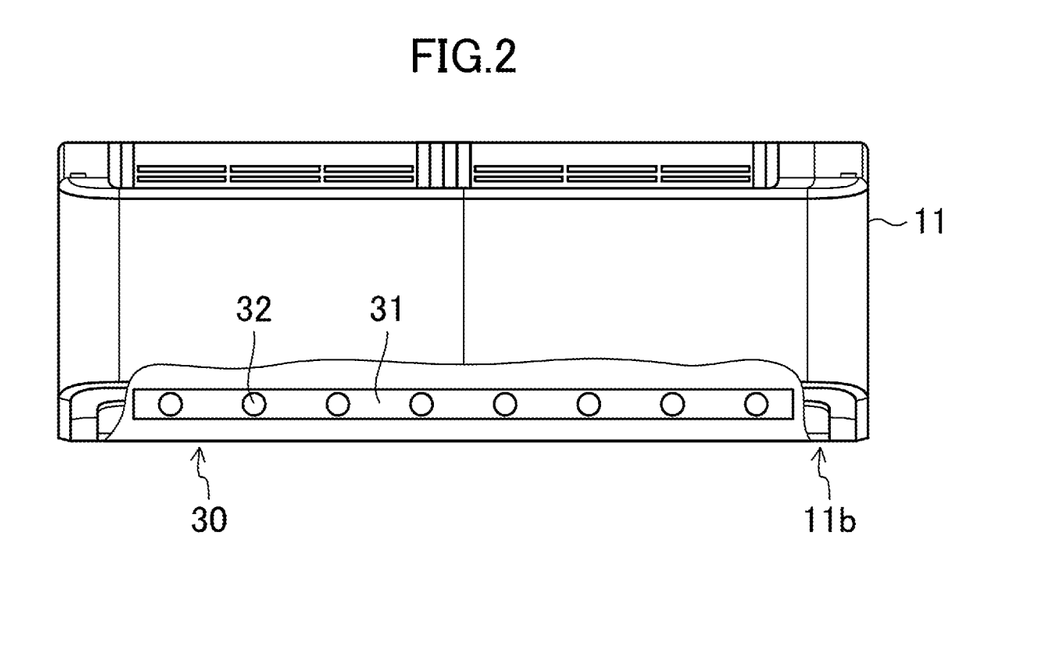
FIG. 2 is a front view of the indoor unit.

The generation unit (30) provides an antimicrobial element to the flap (20). As illustrated in FIGS. 1 and 2, the generation unit (30) is disposed in a lower portion of the interior of the casing (11). The generation unit (30) includes one fixing part (31) and the plurality of generators (32).

The fixing part (31) is a member for fixing the generators (32) inside the casing (11). The fixing part (31) is formed in the shape of a prism elongated in the horizontal direction as viewed from the front. The fixing part (31) extends from one end to the other end of the outlet (11b) along the lengthwise direction of the outlet (11b). The fixing part (31) is disposed between the fan (14) and the flap (20). In other words, the fixing part (31) is disposed in the blow-out flow path (41). The fixing part (31) is disposed generally at the center of the outlet (11b) in the width direction orthogonal to the lengthwise direction of the outlet (11b) as viewed from the outlet (11b).

The generators (32) generate the antimicrobial element that sanitizes the flap (20), and releases the generated antimicrobial element to their surrounding areas. In this embodiment, the antimicrobial element is ultraviolet light. The generators (32) are light sources that generate ultraviolet light. Specifically, the generators (32) are light emitting diodes (LEDs). The generators (32) are arranged at equal intervals in the lengthwise direction of the outlet (11b). The generators (32) are arranged to emit ultraviolet light toward the outlet (11b).

In the first position in which the first surface (23) of the flap body (21) is opposed to the generators (32), the antimicrobial element is provided to the first surface (23) of the flap body (21). In the second position in which the second surface (24) of the flap body (21) is opposed to the generators (32), the antimicrobial element is provided to the second surface (24) of the flap body (21).

<Control Unit>

Figure 3:
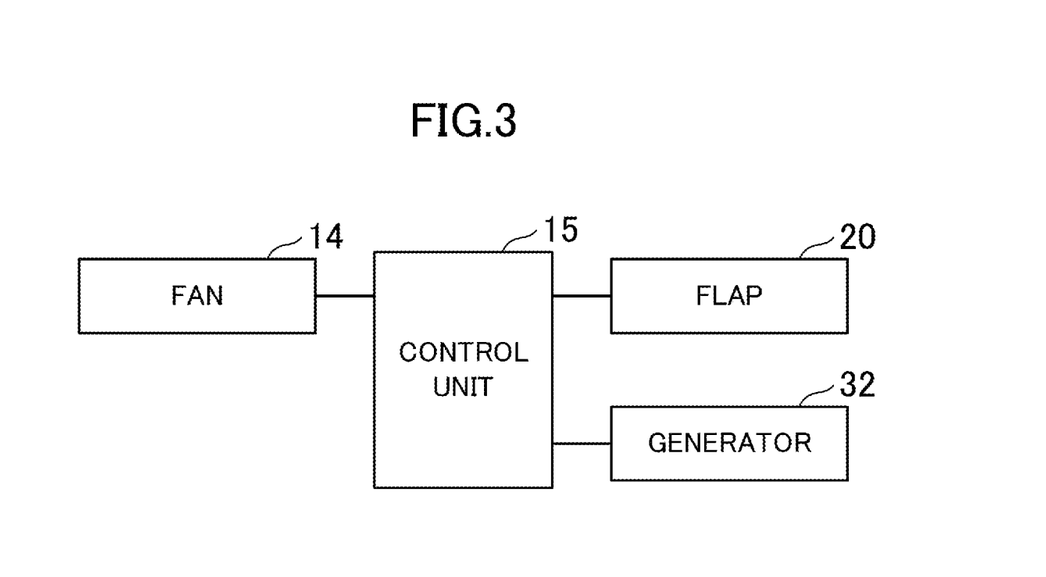
FIG. 3 is a block diagram showing the relationship between a control unit and its peripheral devices.

The control unit (15) shown in FIG. 3 includes a microcomputer and a memory device (specifically, a semiconductor memory). The memory device stores software for operating the microcomputer. The control unit (15) is connected to the fan (14), the flap (20), and the generators (32) via wires. Signals are exchanged between these components and the control unit (15). The control unit (15) processes signals from a remote controller (not shown), controls the fan (14), the flap (20), and the generators (32), and performs other operations.

—Basic Operation—

A basic operation of the indoor unit (1) will be described. The air conditioner (100) performs a blow-out operation of blowing air out of the outlet (11b). The blow-out operation includes a cooling operation of cooling indoor air and a heating operation of heating indoor air.

The cooling operation performed in response to the user's handling of the remote controller causes the control unit (15) to rotate the flap (20) from the first position to open the outlet (11b) and to operate the fan (14) after the rotation of the flap (20). Operation of the fan (14) allows indoor air to be taken through the inlet (11a) into the internal space (S1). The air taken through the inlet (11a) passes through the filter (12). The filter (12) catches dust and any other substances in the air. The air that has passed through the filter (12) flows through the heat exchanger (13). The air that has flowed into the heat exchanger (13) is cooled by the heat exchanger (13). The cooled air passes through the fan (14), and flows through the blow-out flow path (41). The air in the blow-out flow path (41) is guided forward and downward, and is blown out of the outlet (11b) into the room.

If the heating operation is performed, the indoor unit (1) operates in the same manner as in the cooling operation until air passes through the filter (12). The air that has passed through the filter (12) and that has flowed into the heat exchanger (13) is heated by passing through the heat exchanger (13). The heated air passes through the fan (14), flows through the blow-out flow path (41), and is blown out of the outlet (11b) into the room, just like the cooling operation.

—Operation of Providing Antimicrobial Element—

Next, an operation of providing the antimicrobial element to the flap (20) will be described.

During the blow-out operation of the air conditioner (100), the user handles the remote controller to stop the operation. The control unit (15) that has received a signal for shutdown stops the fan (14), and then rotates the flap (20) to the first position. The flap (20) in the first position blocks the outlet (11b), and the first surface (23) thereof faces the generators (32). The control unit (15) energizes the generators (32) while the first surface (23) faces the generators (32). Energizing the generators (32) causes ultraviolet light generated by the generators (32) to be emitted to the first surface (23) of the flap (20) as illustrated in FIG. 4. The emission of the ultraviolet light allows bacteria, mold spores, and other similar substances deposited on the flap (20) to die out under the ultraviolet light. Thus, the first surface (23) of the flap (20) is sanitized.

Figure 5:
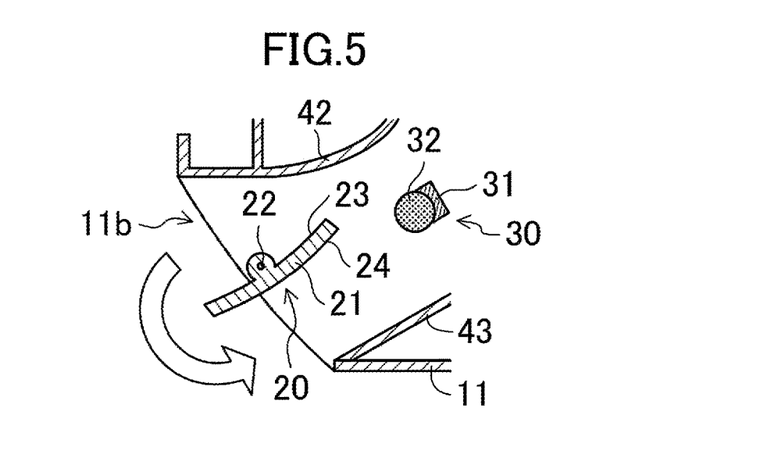
FIG. 5 is an explanatory diagram illustrating the state where the flap is shifting from the first position to a second position.

When a predetermined time has elapsed since the energization of the generators (32), the control unit (15) stops energizing the generators (32) and suspends the emission of ultraviolet light from the generators (32). When the emission of ultraviolet light from the generators (32) is suspended, the control unit (15) rotates the flap (20) by 180° as illustrated in FIG. 5. The flap (20) rotated by 180° is in the second position as illustrated in FIG. 6. Thus, the outlet (11b) is again blocked by the flap (20), and the second surface (24) of the flap (20) faces the generators (32). The control unit (15) energizes the generators (32) while the second surface (24) faces the generators (32). Energizing the generators (32) causes ultraviolet light generated by the generators (32) to be emitted to the second surface (24) of the flap (20). The emission of the ultraviolet light allows bacteria, mold spores, and other similar substances deposited on the flap (20) to die out under the ultraviolet light. Thus, the second surface (24) of the flap (20) is sanitized.

When a predetermined time has elapsed since the energization of the generators (32), the control unit (15) stops energizing the generators (32) and suspends the emission of ultraviolet light from the generators (32). When the emission of ultraviolet light from the generators (32) is suspended, the control unit (15) rotates the flap (20) by 180°. The flap (20) rotated by 180° returns to the first position.

According to the foregoing operation, in the indoor unit (1), ultraviolet light is emitted to both the first and second surfaces (23) and (24) of the flap (20) to sanitize both of these surfaces of the flap (20).

Feature (1) of First Embodiment

The air conditioner (100) of this embodiment includes the generators (32). The generators (32) generate ultraviolet light to sanitize the flap (20). The flap (20) has the first and second surfaces (23) and (24). The flap (20) is shiftable between the first and second positions. In the first position, ultraviolet light is emitted to the first surface (23). In the second position, ultraviolet light is emitted to the second surface (24).

Here, while an air conditioner is operating, cold air flows along both surfaces of a flap of an indoor unit into a room. This may cause condensation on both of these surfaces of the flap. If no measures are taken against the condensation, this condensation causes generation of mold and odorous substances on both of these surfaces of the flap. Work, such as cleaning by wiping, is required to remove such mold and odorous substances, and takes time and effort. If this cleaning work is not performed, air contaminated with mold or any other substances may be supplied into the room, resulting in loss of comfort.

As a measure to address condensation, a chemical agent, such as an antifungal agent, may be applied to both surfaces of the flap. However, this method becomes less effective over time, because the chemical agent deteriorates. To maintain advantages of the chemical agent, the chemical agent may be additionally applied. However, this additional application method takes time, effort, and cost.

To address this problem, since the flap (20) of the air conditioner (100) of this embodiment is shiftable between the first and second positions, the antimicrobial element is provided to both of the first and second surfaces (23) and (24) of the flap (20). Thus, both of these surfaces of the flap (20) are sanitized. This can reduce contamination of both of these surfaces of the flap (20). As a result, the time and effort required to clean the flap (20) can be reduced. In addition, contamination of air blown out of the indoor unit (1) can be reduced. This can reduce a decrease in comfort.

Feature (2) of First Embodiment

The generators (32) of the air conditioner (100) of this embodiment are provided in the casing (11). In the first position, the first surface (23) faces the generators (32). In the second position, the second surface (24) faces the generators (32).

In the first position of this embodiment, the first surface (23) faces the generators (32), and in the second position, the second surface (24) faces the generators (32). This enables efficient sanitization of the entire first and second surfaces (23) and (24).

Feature (3) of First Embodiment

The flap (20) of the air conditioner (100) of this embodiment is capable of opening and closing the outlet (11b). The flap (20) in each of the first and second positions blocks the outlet (11b).

Since the flap (20) in each of the first and second positions of this embodiment blocks the outlet (11b), the antimicrobial element can be substantially prevented from being released from the outlet (11b) to the outside of the casing (11).

Feature (4) of First Embodiment

The antimicrobial element of the air conditioner (100) of this embodiment is ultraviolet light.

Since the antimicrobial element of this embodiment is ultraviolet light, the antimicrobial element can be uniformly provided to the flap body (21).

Feature (5) of First Embodiment

The outlet (11b) of the air conditioner (100) of this embodiment has a rectangular shape. The generators (32) are a plurality of light sources that generate ultraviolet light. The plurality of generators (32) are provided in the lengthwise direction of the outlet (11b).

In this embodiment, the plurality of light sources generating ultraviolet light are provided in the lengthwise direction of the outlet (11b). Thus, the flap body (21) can be sanitized with a simple structure.

Variations of First Embodiment

First Variation

Figure 7:
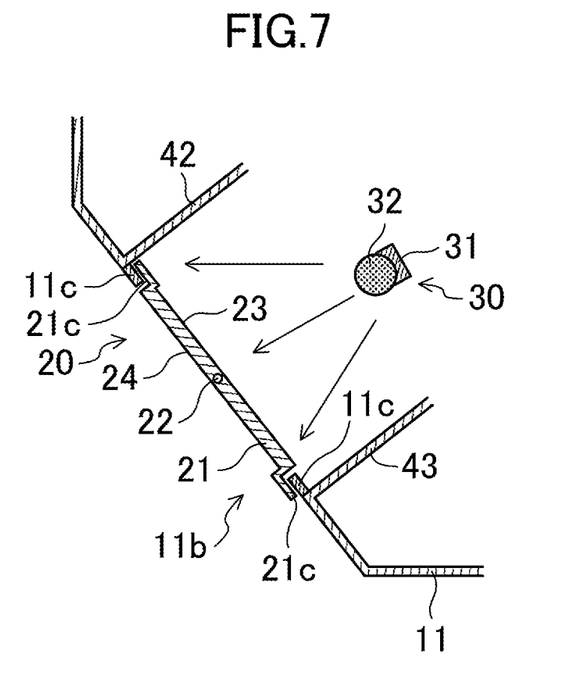
FIG. 7 corresponds to FIG. 4 and illustrates a first variation of the first embodiment.

As illustrated in FIG. 7, in the air conditioner (100) of this embodiment, two protrusions (11c) formed at the outlet (11b) of the casing (11) may overlap with two recesses (21c) formed on the flap body (21) to block the outlet (11b).

Specifically, the protrusions (11c) are formed at upper and lower portions of the outlet (11b). The protrusions (11c) protrude from the upper and lower ends of the outlet (11b) toward the center of the outlet (11b). The protrusions (11c) are formed generally along the entire length of the outlet (11b) in the lengthwise direction thereof. The recesses (21c) are formed at both ends of the flap body (21) in the widthwise direction thereof. Each recess (21c) is formed generally along the entire length of the associated long side of the flap body (21). One of the recesses (21c) is one step lower than the first surface (23). The other recess (21c) is one step lower than the second surface (24).

While the flap body (21) is located in the first position, the recess (21c) at the one end of the flap body (21) in the widthwise direction thereof engages with the upper protrusion (11c), and the recess (21c) at the other end of the flap body (21) in the widthwise direction thereof engages with the lower protrusion (11c). The engagement between the recesses (21c) of the flap body (21) and the corresponding projections (11c) allows the gap between the edge of the outlet (11b) and the flap body (21) to be blocked. This reduces the leakage of the antimicrobial element through the outlet (11b).

Second Variation

Figure 8:
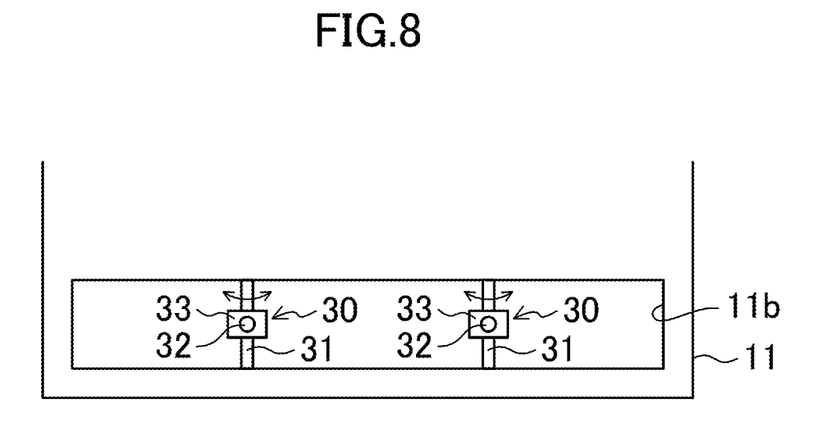
FIG. 8 is a schematic diagram illustrating the layout of light sources according to a second variation of the first embodiment.

As illustrated in FIG. 8, in the air conditioner (100) of this embodiment, a plurality of generation units (30) may be provided, and a generator (32) of each of the generation units (30) may swing.

Specifically, the air conditioner (100) includes two generation units (30). One of the generation units (30) is disposed on the left side of the center of the casing (11), and the other generation unit (30) is disposed on the right side of the center of the casing (11). Each generation unit (30) includes one fixing part (31), one swing part (33), and one generator (32).

The fixing part (31) is a member for fixing the one generator (32) inside the casing (11). The fixing part (31) is formed in the shape of a prism extending generally in the perpendicular direction as viewed from the outlet (lib). The generator (32) is attached to the swing part (33). The swing part (33) changes the direction in which ultraviolet light is emitted from the generator (32). The swing part (33) is configured such that the generator (32) swings in the side-to-side directions. The swing part (33) is attached to the center of the fixing part (31).

In the operation of providing the antimicrobial element to the flap (20), the swing parts (33) of the generation units (30) swing in the side-to-side directions until a predetermined time has elapsed since the energization of the generators (32). This allows ultraviolet light generated by the generators (32) to be emitted to the entire first and second surfaces (23) and (24) of the flap (20).

Second Embodiment

A second embodiment will be described below. An air conditioner (100) of this embodiment is a modified version, of the air conditioner (100) of the first embodiment, in which the configurations of the flap (20) and the generation unit (30) have been changed. Thus, the following description will be focused on the differences between the air conditioner (100) of this embodiment and the air conditioner (100) of the first embodiment.

—Flap—

Figure 9:
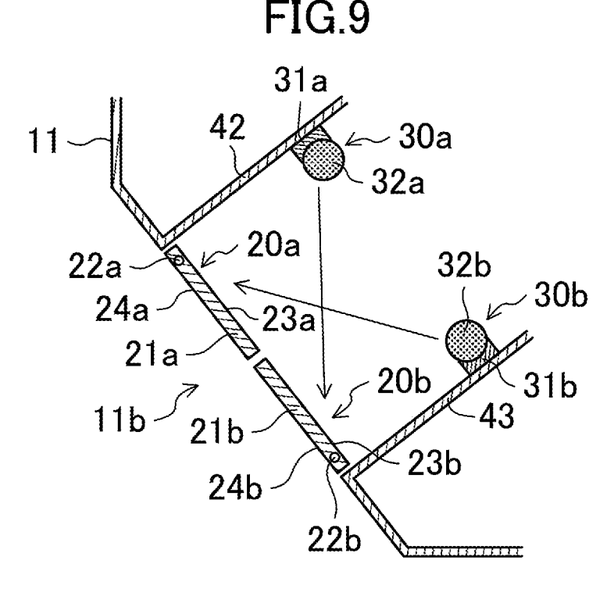
FIG. 9 corresponds to FIG. 4 and illustrates a second embodiment.

As illustrated in FIG. 9, two flaps (20) are provided at an outlet (11b) of a casing (11). The two flaps (20a, 20b) include an upper flap (20a) disposed on the upper side of the outlet (11b), and a lower flap (20b) disposed on the lower side of the outlet (11b). The upper and lower flaps (20a) and (20b) each have a flap body (21a, 21b) and a shaft (22a, 22b).

The shaft (22a) of the upper flap (20a) is disposed at an end of the upper flap body (21a) near the casing (11). The shaft (22a) of the upper flap (20a) is disposed at an upper portion of the outlet (11b) of the casing (11). The shaft (22b) of the lower flap (20b) is disposed at an end of the lower flap body (21b) near the casing (11). The shaft (22b) of the lower flap (20b) is disposed at a lower portion of the outlet (11b) of the casing (11). The flap body (21a) of the upper flap (20a) rotates around the shaft (22a). The flap body (21b) of the lower flap (20b) rotates around the shaft (22b).

The upper and lower flaps (20a, 20b) are configured as double doors (biparting doors) to be capable of opening and closing the outlet (11b). Specifically, the upper flap (20a) rotating around the shaft (22a) from its orientation along the outlet (11b) in the counterclockwise direction in FIG. 9 causes a first surface (23a) of the upper flap (20a) to shift toward the inside of the casing (11). The lower flap (20b) rotating around the shaft (22b) from its orientation along the outlet (11b) in the clockwise direction in FIG. 9 causes a first surface (23b) of the lower flap (20b) to shift toward the inside of the casing (11). The upper and lower flaps (20a, 20b) shifting toward the inside of the casing (11) as described above causes the outlet (11b) to open.

The upper flap (20a) rotating around the shaft (22a) from its orientation along the outlet (11b) in the clockwise direction in FIG. 9 causes a second surface (24a) of the upper flap (20a) to shift toward the outside of the casing (11). The lower flap (20b) rotating around the shaft (22b) from its orientation along the outlet (11b) in the counterclockwise direction in FIG. 9 causes a second surface (24b) of the lower flap (20b) to shift toward the outside of the casing (11). The upper and lower flaps (20a, 20b) shifting toward the outside of the casing (11) as described above also causes the outlet (11b) to open.

In a first position, the flaps (20a, 20b) are both oriented along the outlet (11b), and the flaps (20) block the outlet (11b). A second position is a position in which the upper flap (20a) is rotated by about 90° from the first position in the counterclockwise direction in FIG. 9 and the lower flap (20b) is rotated by about 90° from the first position in the clockwise direction in FIG. 9. In other words, the second position is a position in which the upper and lower flap bodies (21a, 21b) are each rotated by about 90° from the first position to enter the casing (11).

—Generation Unit—

The air conditioner (100) includes two generation units (30). The two generation units (30) include an upper generation unit (30a) and a lower generation unit (30b). The configuration of each generation unit (30) is the same as, or similar to, that of the first embodiment.

A fixing part (31a) of the upper generation unit (30a) is disposed on the back side of the upper flap (20a) (toward a fan). Specifically, the fixing part (31a) of the upper generation unit (30a) is disposed on a surface of a front side wall (42) near a blow-out flow path (41). A fixing part (31b) of the lower generation unit (30b) is disposed on the back side of the lower flap (20b) (toward the fan). Specifically, the fixing part (31b) of the lower generation unit (30b) is disposed on a surface of a rear side wall (43) near the blow-out flow path (41).

While the air conditioner (100) is at rest, a generator (32a) of the upper generation unit (30a) is disposed to face the first surface (23b) of the lower flap (20b). While the air conditioner (100) is at rest, a generator (32b) of the lower generation unit (30b) is disposed to face the first surface (23a) of the upper flap (20a).

Figure 10:
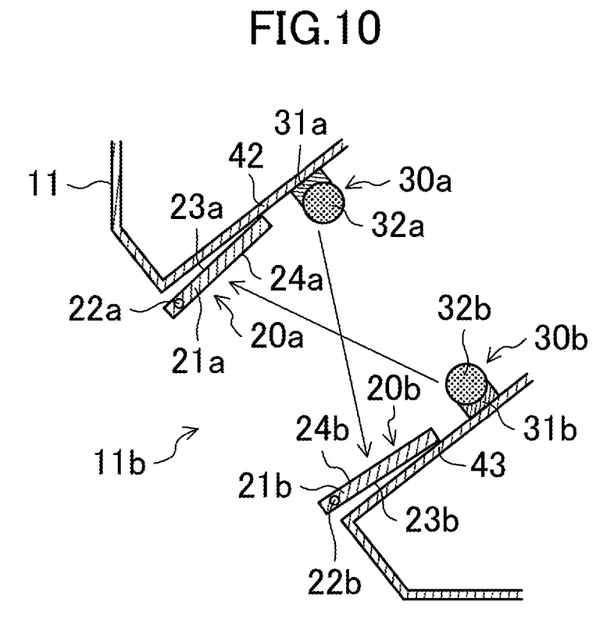
FIG. 10 corresponds to FIG. 6 and illustrates the second embodiment.

As illustrated in FIG. 9, in the first position, the first surface (23a) of the upper flap body (21a) and the lower generator (32b) face each other, and the first surface (23b) of the lower flap body (21b) and the upper generator (32a) face each other. As illustrated in FIG. 10, in the second position, the second surface (24a) of the upper flap body (21a) and the lower generator (32b) face each other, and the second surface (24b) of the lower flap body (21b) and the upper generator (32a) face each other.

—Operation of Providing Antimicrobial Element—

Next, an operation of providing an antimicrobial element to the flaps (20) according to the second embodiment will be described. This operation is the same as, or similar to, that of the first embodiment from when a blow-out operation of the air conditioner (100) is stopped to when the outlet (11b) is blocked.

While the first surface (23a) of the upper flap body (21a) and the lower generator (32b) face each other, and the first surface (23b) of the lower flap body (21b) and the upper generator (32a) face each other, the control unit (15) energizes the generators (32a, 32b). Energizing the generators (32a, 32b) causes ultraviolet light generated by the generators (32a, 32b) to be emitted to the first surfaces (23a, 23b) of the upper and lower flaps (20a) and (20b) as illustrated in FIG. 9. The emission of the ultraviolet light allows bacteria, mold spores, and other similar substances deposited on the upper and lower flaps (20a) and (20b) to die out under the ultraviolet light. Thus, the first surfaces (23a, 23b) of the upper and lower flaps (20a) and (20b) are sanitized.

When a predetermined time has elapsed since the energization of the generators (32a, 32b), the control unit (15) stops energizing the generators (32a, 32b) and suspends the emission of ultraviolet light from the generators (32a, 32b). When the emission of ultraviolet light from the generators (32a, 32b) is suspended, the control unit (15) rotates the upper and lower flaps (20a) and (20b) by about 90°. As illustrated in FIG. 10, the upper and lower flaps (20a) and (20b) rotating by about 90° causes the upper and lower flaps (20a) and (20b) to be in the second position, causes the second surface (24a) of the upper flap (20a) to face the lower generator (32b), and causes the second surface (24b) of the lower flap (20b) to face the upper generator (32a). The control unit (15) energizes the generators (32a, 32b) while the second surfaces (24a, 24b) face the corresponding generators (32a, 32b). Energizing the generators (32a, 32b) allows ultraviolet light generated by the generators (32a, 32b) to be emitted to the second surfaces (24a, 24b) of the upper and lower flaps (20a) and (20b). Thus, the second surfaces (24a, 24b) of the upper and lower flaps (20a) and (20b) that have received the ultraviolet light are sanitized.

When a predetermined time has elapsed since the energization of the generators (32a, 32b), the control unit (15) stops energizing the generators (32a, 32b) and suspends the emission of ultraviolet light from the generators (32a, 32b). When the emission of ultraviolet light from the generators (32a, 32b) is suspended, the control unit (15) rotates the upper and lower flaps (20a) and (20b) by about 90°. The rotation of the upper and lower flaps (20a) and (20b) causes the upper and lower flaps (20a) and (20b) to return to the first position.

Third Embodiment

A third embodiment will be described below. An air conditioner (100) of this embodiment is a modified version, of the air conditioner (100) of the first embodiment, in which the configurations of the flap (20) and the generation unit (30) have been changed. Thus, the following description will be focused on the differences between the air conditioner (100) of this embodiment and the air conditioner (100) of the first embodiment.

—Flap—

Figure 11:
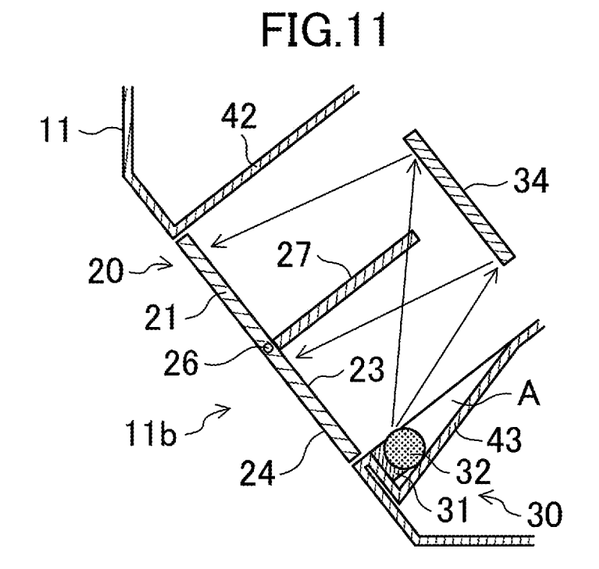
FIG. 11 corresponds to FIG. 4 and illustrates a third embodiment.

As illustrated in FIG. 11, a flap (20) includes one flap body (21), one slide shaft (26), and two rails (27). The slide shaft (26) is provided on the center of the flap body (21) to pass through the flap body (21). The slide shaft (26) is provided generally parallel to the lengthwise direction of the flap body (21). In other words, the slide shaft (26) is disposed at the center of an outlet (11b).

The rails (27) are used to shift the flap body (21) in parallel. The rails (27) are each provided on a corresponding one of right and left inner surfaces of a casing (11). The rails (27) are positioned generally orthogonal to the flap body (21). The slide shaft (26) shifts along the rails (27).

FIG. 11 illustrates a state where the flap body (21) blocks the outlet (11b). As illustrated in FIG. 11, a first surface (23) of the flap body (21) faces the inside of the casing (11). A second surface (24) of the flap body (21) faces the outside of the casing (11). In a first position, the flap (20) blocks the outlet (11b). A second position is a position in which the flap body (21) is shifted in parallel from the first position toward the inside of the casing (11) by a predetermined distance.

—Generation Unit—

A generation unit (30) includes one fixing part (31), a plurality of generators (32), and one reflector (34). The fixing part (31) is disposed in a housing space (A) formed behind the outlet (11b) of the casing (11). The housing space (A) is formed in a lower portion of a rear side wall (43) of a flow path forming portion (40). The housing space (A) is formed as a portion of the rear side wall (43) recessed rearward. The housing space (A) is formed in a substantially triangular shape as viewed from a side surface of the casing (11). The housing space (A) extends from one end to the other end of the outlet (11b) along the lengthwise direction of the outlet (11b).

Figure 12:
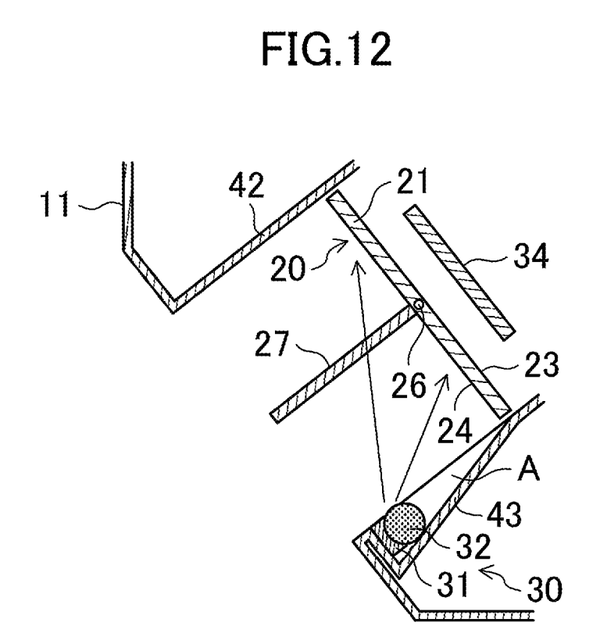
FIG. 12 corresponds to FIG. 6 and illustrates the third embodiment.

The reflector (34) receives an antimicrobial element generated by the generators (32), and reflects the received antimicrobial element toward the first surface (23) of the flap body (21). The reflector (34) is a plate-shaped member. The reflector (34) is disposed between a fan (14) and the flap (20). The reflector (34) is disposed generally parallel to the flap body (21). The reflector (34) is opposed to the first surface (23) of the flap body (21). As illustrated in FIG. 11, in the first position, the antimicrobial element is provided via the reflector (34) to the first surface (23) of the flap body (21). As illustrated in FIG. 12, in the second position, the antimicrobial element is provided to the second surface (24) of the flap body (21).

—Operation of Providing Antimicrobial Element—

Next, an operation of providing the antimicrobial element to the flap (20) according to the third embodiment will be described. This operation is the same as, or similar to, that of the first embodiment from when a blow-out operation of the air conditioner (100) is stopped to when the outlet (11b) is blocked.

The control unit (15) energizes the generators (32) while the flap (20) is located in the first position. Energizing the generators (32) causes ultraviolet light generated by the generators (32) to be released to their surrounding areas as illustrated in FIG. 11. The released ultraviolet light is reflected by the reflector (34) so as to be emitted to the first surface (23) of the flap (20). The emission of the ultraviolet light allows bacteria, mold spores, and other similar substances deposited on the flap (20) to die out under the ultraviolet light. Thus, the first surface (23) of the flap (20) is sanitized.

When a predetermined time has elapsed since the energization of the generators (32), the control unit (15) stops energizing the generators (32) and suspends the emission of ultraviolet light from the generators (32). When the emission of ultraviolet light from the generators (32) is suspended, the control unit (15) shifts the flap (20) to the second position.

The control unit (15) energizes the generators (32) while the flap (20) is located in the second position. Energizing the generators (32) causes ultraviolet light generated by the generators (32) to be released to their surrounding areas as illustrated in FIG. 12. The released ultraviolet light is emitted to the second surface (24) of the flap (20). Thus, the second surface (24) of the flap (20) that has received the ultraviolet light is sanitized.

When a predetermined time has elapsed since the energization of the generators (32), the control unit (15) stops energizing the generators (32) and suspends the emission of ultraviolet light from the generators (32). When the emission of ultraviolet light from the generators (32) is suspended, the control unit (15) shifts the flap (20) to the first position.

Fourth Embodiment

A fourth embodiment will be described below. An air conditioner (100) of this embodiment is a modified version, of the air conditioner (100) of the first embodiment, in which the configuration of the flow path forming portion (40) and the arrangement of the generation unit (30) are changed. Thus, the following description will be focused on the differences between the air conditioner (100) of this embodiment and the air conditioner (100) of the first embodiment.

—Flow Path Forming Portion—

Figure 13:
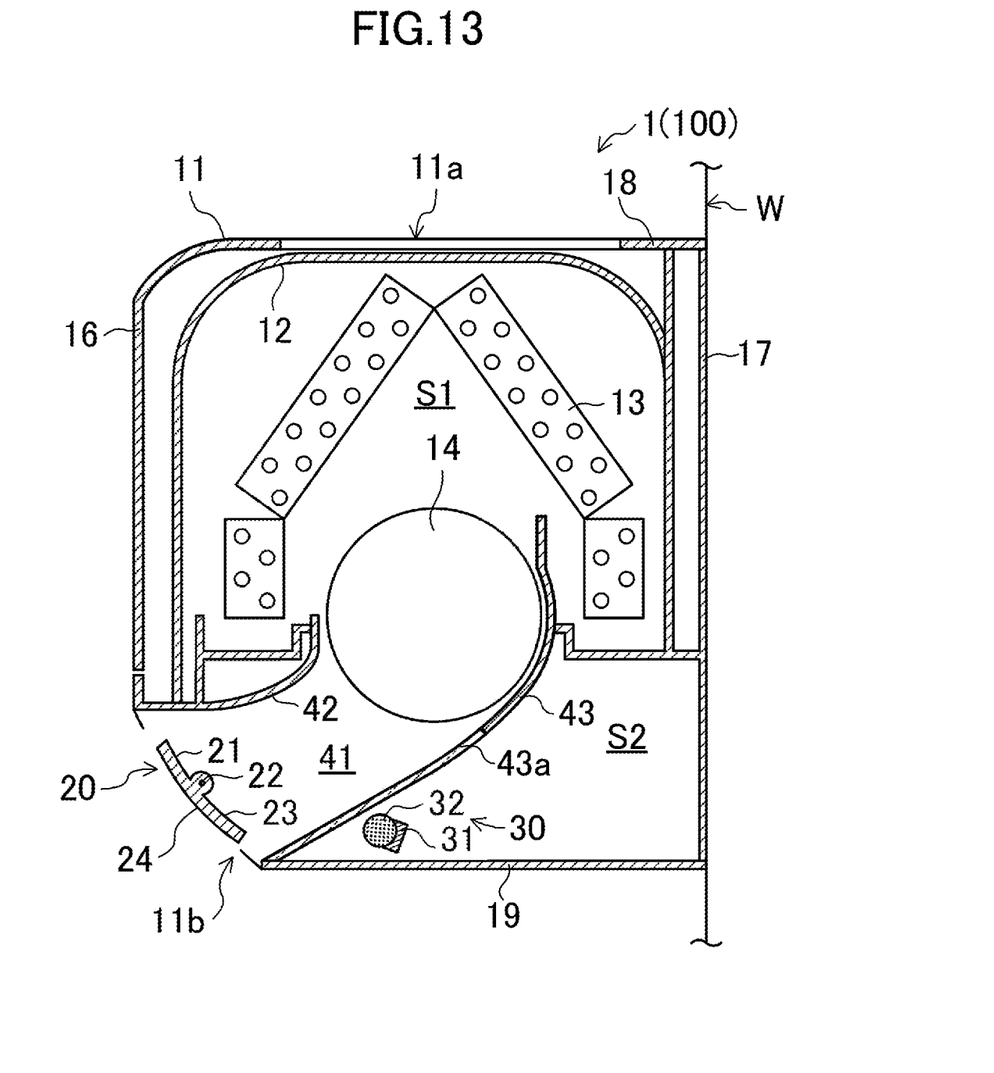
FIG. 13 corresponds to FIG. 1 and illustrates a fourth embodiment.

As illustrated in FIG. 13, a rear side wall (43) of a flow path forming portion (40) has a transparent portion (43a). The transparent portion (43a) is made of a material transparent to ultraviolet light with predetermined wavelengths. The transparent portion (43a) of this embodiment is made of a material transmitting ultraviolet light with wavelengths from 200 nm to 230 nm (e.g., glass). The transparent portion (43a) is formed as a portion of the rear side wall (43) below a fan (14). The transparent portion (43a) extends from one end to the other end of an outlet (11b) along the lengthwise direction (the side-to-side direction) of the outlet (11b). The configuration of a front side wall (42) is the same as, or similar to, that of the first embodiment.

—Flap—

In this embodiment, a second position of the flap (20) is different from that of the first embodiment. Specifically, as illustrated in FIG. 15, the second position is a position in which a second surface (24) of a flap body (21) faces the transparent portion (43a). In other words, in the second position, the second surface (24) of the flap body (21) faces generators (32). This second position is a position in which the flap body (21) is rotated by about 90° from the first position in the counterclockwise direction in FIG. 14. In the second position, the flap body (21) is located generally perpendicular to the outlet (11b). In the second position, the outlet (11b) is opened.

—Generation Unit—

A generation unit (30) is disposed near the front end of a pipe space (S2). The generation unit (30) is disposed below the transparent portion (43a) of the rear side wall (43). Specifically, the generation unit (30) is disposed between the transparent portion (43a) and a bottom panel (19). The generation unit (30) is disposed outside a blow-out flow path (41).

The generators (32) are light sources that generate ultraviolet light as an antimicrobial element. The generators (32) are disposed to emit ultraviolet light toward the outlet (11b) and the front side wall (42). The antimicrobial element of this embodiment is ultraviolet light including ultraviolet light with wavelengths from 200 nm to 230 nm. In one preferred embodiment, the antimicrobial element includes ultraviolet light with a wavelength of 222 nm.

Here, ultraviolet light with wavelengths from 200 nm to 230 nm has less influence on deterioration of a component made of a resin than ultraviolet light with wavelengths except the wavelengths from 200 nm to 230 nm. For this reason, using ultraviolet light with wavelengths from 200 nm to 230 nm as an antimicrobial element can reduce deterioration of a component which is made of a resin and on which ultraviolet light with such wavelengths is incident.

In addition, ultraviolet light with wavelengths from 200 nm to 230 nm has a small influence also on human bodies. For this reason, using ultraviolet light with wavelengths from 200 nm to 230 nm as an antimicrobial element allows ultraviolet light to be emitted while the flap (20) does not completely block the outlet (11b). The antimicrobial element generated by the generators (32) of this embodiment may include ultraviolet light with wavelengths except the wavelengths from 200 nm to 230 nm.

—Operation of Providing Antimicrobial Element—

Next, an operation of providing an antimicrobial element to the flap (20) according to the fourth embodiment will be described. This operation is the same as, or similar to, that of the first embodiment from when a blow-out operation of the air conditioner (100) is stopped to when emission of ultraviolet light from the generators (32) is suspended after the lapse of a predetermined time since sanitization of the first surface (23) of the flap (20).

Figure 14:
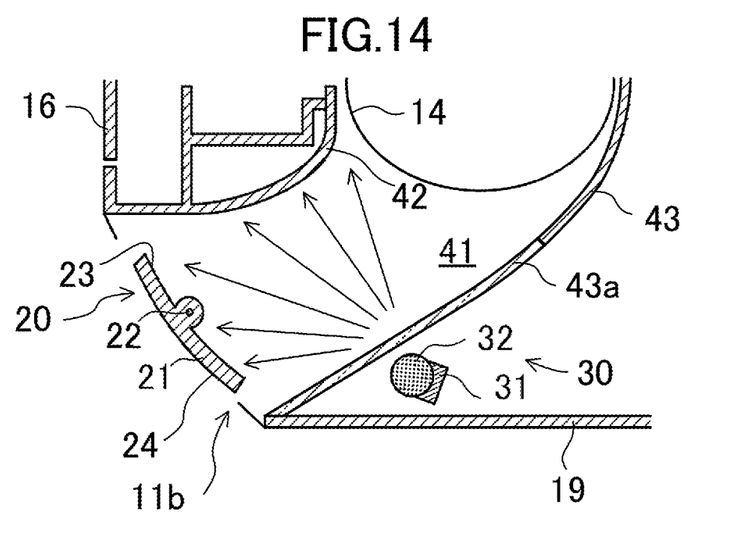
FIG. 14 corresponds to FIG. 4 and illustrates the fourth embodiment.
Figure 15:
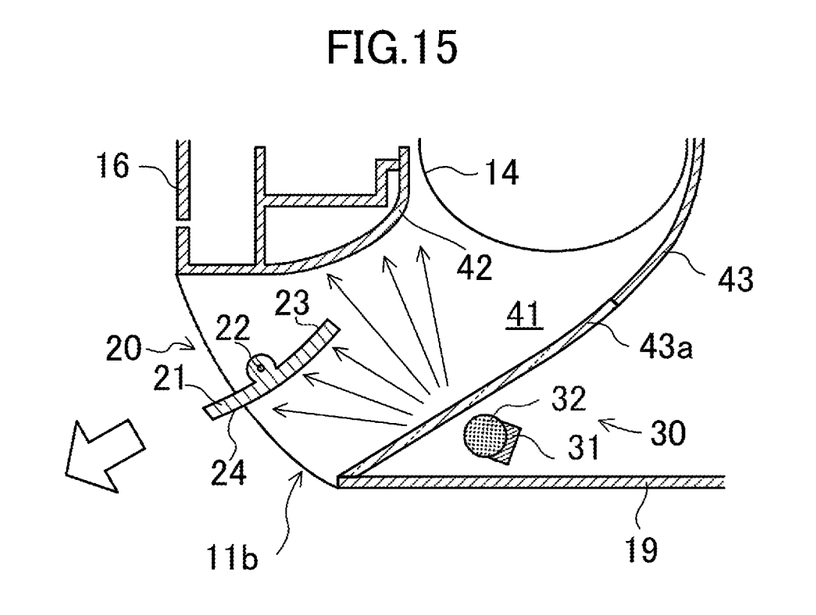
FIG. 15 corresponds to FIG. 6 and illustrates the fourth embodiment.

If, after the emission of ultraviolet light to the first surface (23) of the flap (20) has been suspended, the blow-out operation of the air conditioner (100) is again performed, a control unit (15) rotates the flap (20) by about 90° in the counterclockwise direction in FIG. 14. As illustrated in FIG. 15, the flap (20) shifts to the second position. Thus, the outlet (11b) is opened, and the second surface (24) of the flap (20) faces the generators (32). The flap (20) in the second position allows the control unit (15) to rotate the fan (14), thereby blowing air with its temperature controlled by a heat exchanger (13) out of the outlet (11b). When the air is blown out of the outlet (11b), the control unit (15) energizes the generators (32) while the second surface (24) of the flap (20) faces the generators (32).

Energizing the generators (32) causes the generators (32) to generate ultraviolet light, which is transmitted through the transparent portion (43a) of the rear side wall (43) so as to be emitted to the second surface (24) of the flap (20), the front side wall (42), and air passing through the blow-out flow path (41). The emission of the ultraviolet light allows bacteria, mold spores, and other similar substances deposited on the second surface (24) of the flap (20) and the front side wall (42) or contained in the air passing through the blow-out flow path (41) to die out under the ultraviolet light. Thus, the second surface (24) of the flap (20), the front side wall (42), and the air passing through the blow-out flow path (41) are sanitized.

When a predetermined time has elapsed since the energization of the generators (32), the control unit (15) stops energizing the generators (32) and suspends the emission of ultraviolet light from the generators (32). When a predetermined time has elapsed since the energization of the generators (32) is stopped, the generators (32) are again energized to emit ultraviolet light to the second surface (24) of the flap (20), the front side wall (42), and the air passing through the blow-out flow path (41).

As can be seen, during the blow-out operation, the generators (32) emit ultraviolet light to the air blown out of the outlet (11b). Thus, the air blown out of the outlet (11b) can be sanitized. In addition, the generators (32) emit ultraviolet light also to the front side wall (42).

Thus, the blow-out flow path (41) can also be sanitized.

Other Embodiments

The above-described embodiments may be modified as follows.

The air treatment device of each of the foregoing embodiments is not limited to an air conditioner (100) configured to condition air in a room. The air treatment device may be, for example, a humidity control apparatus configured to control the humidity of a target space or an air cleaner configured to clean air in a target space.

The air conditioner (100) of each of the foregoing embodiments is a wall-mounted air conditioner, but may be a ceiling-embedded air conditioner.

The indoor unit (1) of each of the foregoing embodiments may include a plurality of perpendicular flaps. The perpendicular flaps are blade-shaped members generally perpendicular to the outlet (11b). In this case, a light source is disposed between each adjacent pair of the perpendicular flaps.

The flap (20) of each of the foregoing embodiment may include a plurality of flaps. In this case, the short sides of the flaps (20) may have different lengths.

The generation unit(s) (30) of each of the foregoing embodiments does not have to include the fixing part (31), and the generators (32) may be disposed directly on the casing (11).

The fixing part (31) of the first embodiment may be disposed above or below the outlet (11b) as viewed from the outlet (11b).

The generators (32) of each of the foregoing embodiments may swing in the top-to-bottom direction or in the side-to-side direction.

The number of the generators (32) of each of the foregoing embodiments is two or more. However, one generator (32) may be provided, and may shift in parallel in the side-to-side direction.

The antimicrobial element of each of the foregoing embodiments may be ozone. In this case, a jet orifice for the antimicrobial element merely needs to be located inside the casing (11).

The antimicrobial element of each of the foregoing embodiments may be hydrogen peroxide or chloric acid.

While the embodiments and variations thereof have been described above, it will be understood that various changes in form and details may be made without departing from the spirit and scope of the claims. The foregoing embodiments and variations thereof may be combined and replaced with each other without deteriorating the intended functions of the present disclosure.

INDUSTRIAL APPLICABILITY

As can be seen from the foregoing description, the present disclosure is useful for an air treatment device.

EXPLANATION OF REFERENCES

100 Air Conditioner (Air Treatment Device)
11 Casing
11a Inlet
11b Outlet
21 Flap Body (Blade)
23 First Surface
24 Second Surface
32 Generator

The invention claimed is:

1. An air treatment device, comprising:
a casing having an inlet through which air is drawn, and an outlet out of which the air drawn through the inlet is blown; and
a blade configured to adjust a flow direction of the air blown out of the outlet,
the air treatment device further comprising: a generator configured to generate an antimicrobial element that sanitizes the blade,
the blade having a first surface, and a second surface opposite to the first surface,
the blade being shiftable between a first position in which the antimicrobial element is provided to the first surface and a second position in which the antimicrobial element is provided to the second surface.

2. The air treatment device of claim 1, wherein
the generator is provided in the casing,
the first surface and the generator face each other in the first position, and
the second surface and the generator face each other in the second position.

3. The air treatment device of claim 1, wherein
the blade is capable of opening and closing the outlet, and in the first and second positions, the blade blocks the outlet.

4. The air treatment device of claim 1, wherein
the antimicrobial element is ultraviolet light or ozone.

5. The air treatment device of claim 4, wherein
the outlet has a rectangular shape,
the generator is a light source that generates the ultraviolet light, and
the generator includes a plurality of generators, the plurality of generators being arranged in a lengthwise direction of the outlet.

6. The air treatment device of claim 1, wherein
the generator generates ultraviolet light with wavelengths from 200 nm to 230 nm as the antimicrobial element.

7. The air treatment device of claim 6, wherein
during an operation of blowing air out of the outlet, the generator emits the ultraviolet light as the antimicrobial element to the air blown out of the outlet.

8. The air treatment device of claim 2, wherein
the blade is capable of opening and closing the outlet, and in the first and second positions, the blade blocks the outlet.

9. The air treatment device of claim 2, wherein
the antimicrobial element is ultraviolet light or ozone.

10. The air treatment device of claim 3, wherein
the antimicrobial element is ultraviolet light or ozone.

11. The air treatment device of claim 2, wherein
the generator generates ultraviolet light with wavelengths from 200 nm to 230 nm as the antimicrobial element.

12. The air treatment device of claim 8, wherein
the antimicrobial element is ultraviolet light or ozone.

13. The air treatment device of claim 9, wherein
the outlet has a rectangular shape,
the generator is a light source that generates the ultraviolet light, and
the generator includes a plurality of generators, the plurality of generators being arranged in a lengthwise direction of the outlet.

14. The air treatment device of claim 10, wherein
the outlet has a rectangular shape,
the generator is a light source that generates the ultraviolet light, and
the generator includes a plurality of generators, the plurality of generators being arranged in a lengthwise direction of the outlet.

15. The air treatment device of claim 11, wherein
during an operation of blowing air out of the outlet, the generator emits the ultraviolet light as the antimicrobial element to the air blown out of the outlet.

16. The air treatment device of claim 12, wherein
the outlet has a rectangular shape,
the generator is a light source that generates the ultraviolet light, and
the generator includes a plurality of generators, the plurality of generators being arranged in a lengthwise direction of the outlet.

* * * * *